US00PP36129P2

(12) United States Plant Patent
Masor

(10) Patent No.: US PP36,129 P2
(45) Date of Patent: Sep. 17, 2024

(54) ***CALIBRACHOA* PLANT NAMED 'Balchaelink'**

(50) Latin Name: ***Calibrachoa* x *hybrida***
Varietal Denomination: Balchaelink

(71) Applicant: Ball Horticultural Company, West Chicago, IL (US)

(72) Inventor: Laura L. Masor, Buda, TX (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/516,443

(22) Filed: Nov. 21, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/00; A01H 6/821; A01H 6/82
See application file for complete search history.

(56) References Cited

PUBLICATIONS

Ballseed Plant Information Cha-Cha Electric Pink Calibrachoa retrieved on Mar. 21, 2024 at https://www.ballseed.com/webtrackplantinfo.aspx?phid=066007114001678&ENV=P, 2 pp. (Year: 2024).*

* cited by examiner

*Primary Examiner* — June Hwu
(74) *Attorney, Agent, or Firm* — Audrey Charles

(57) ABSTRACT

A new and distinct cultivar of *Calibrachoa* plant named 'Balchaelink', characterized by its deep reddish-purple and white colored flowers having a bright yellow base and throat opening, medium green-colored foliage, and vigorous, mounded-trailing growth habit, is disclosed.

1 Drawing Sheet

Latin name of genus and species of plant claimed: *Calibrachoa* x *hybrida*.

Variety denomination: 'Balchaelink'.

BACKGROUND OF THE INVENTION

The present invention relates to a new and distinct cultivar of *Calibrachoa* plant botanically known as *Calibrachoa* x *hybrida* and hereinafter referred to by the cultivar name 'Balchaelink'.

The new cultivar originated in a controlled breeding program in Arroyo Grande, California during May 2018. The objective of the breeding program was the development of *Calibrachoa* cultivars with attractive novelty flower coloration, and a vigorous, mounded-trailing growth habit.

The new *Calibrachoa* cultivar is the result of cross-pollination. The female (seed) parent of the new cultivar is the proprietary *Calibrachoa* x *hybrida* breeding selection coded CAL-16249-01, not patented, characterized by its medium pink, yellow, and white mottled colored flowers, medium green-colored foliage, and vigorous, spreading growth habit. The male (pollen) parent of the new cultivar is SUPERBELLS Holy Cow! 'BBCAL85303', U.S. Plant Pat. No. 30,840, characterized by its red-purple colored petals with white-colored margins, star-shaped pattern and bright yellow-colored centers, medium green-colored foliage, and moderately vigorous, compact, upright to outwardly spreading and mounding to trailing plant habit. The new cultivar was selected as a single flowering plant within the progeny of the above stated cross-pollination during April 2019 in a controlled environment in Arroyo Grande, California.

Asexual reproduction of the new cultivar by terminal stem cuttings since April 2019 in Arroyo Grande, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balchaelink' as a new and distinct cultivar of *Calibrachoa* plant:

1. Deep reddish-purple and white colored flowers having a bright yellow base and throat opening;
2. Medium green-colored foliage; and
3. Vigorous, mounded-trailing growth habit.

Plants of the new cultivar differ from plants of the female parent primarily in having a flower color that is darker pink colored, increased growth vigor and a more mounded growth habit. Plants of the new cultivar differ from plants of the male parent primarily in having darker reddish-purple colored flowers with a greater amount of white coloration and increased growth vigor.

Of the many commercially available *Calibrachoa* cultivars, the most similar in comparison to the new cultivar is Cha-Cha Diva Hot Pink 'Balchadotin', U.S. Plant Pat. No. 32,611. However, in side-by-side comparisons, plants of the new cultivar differ from plants of 'Balchadotin' in at least the following characteristics:

1. Plants of the new cultivar have a flower color that has a darker and more pronounced reddish-purple than plants of 'Balchadotin'; and
2. Plants of the new cultivar have a larger corolla diameter than plants of 'Balchadotin'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balchaelink'. The approximately 4-month-old plants were grown in 3-gallon containers for approximately 8 weeks in an outdoor nursery in West Chicago, Ill. Treatments are described below in the Detailed Botanical Description.

DETAILED BOTANICAL DESCRIPTION

Figure 1:
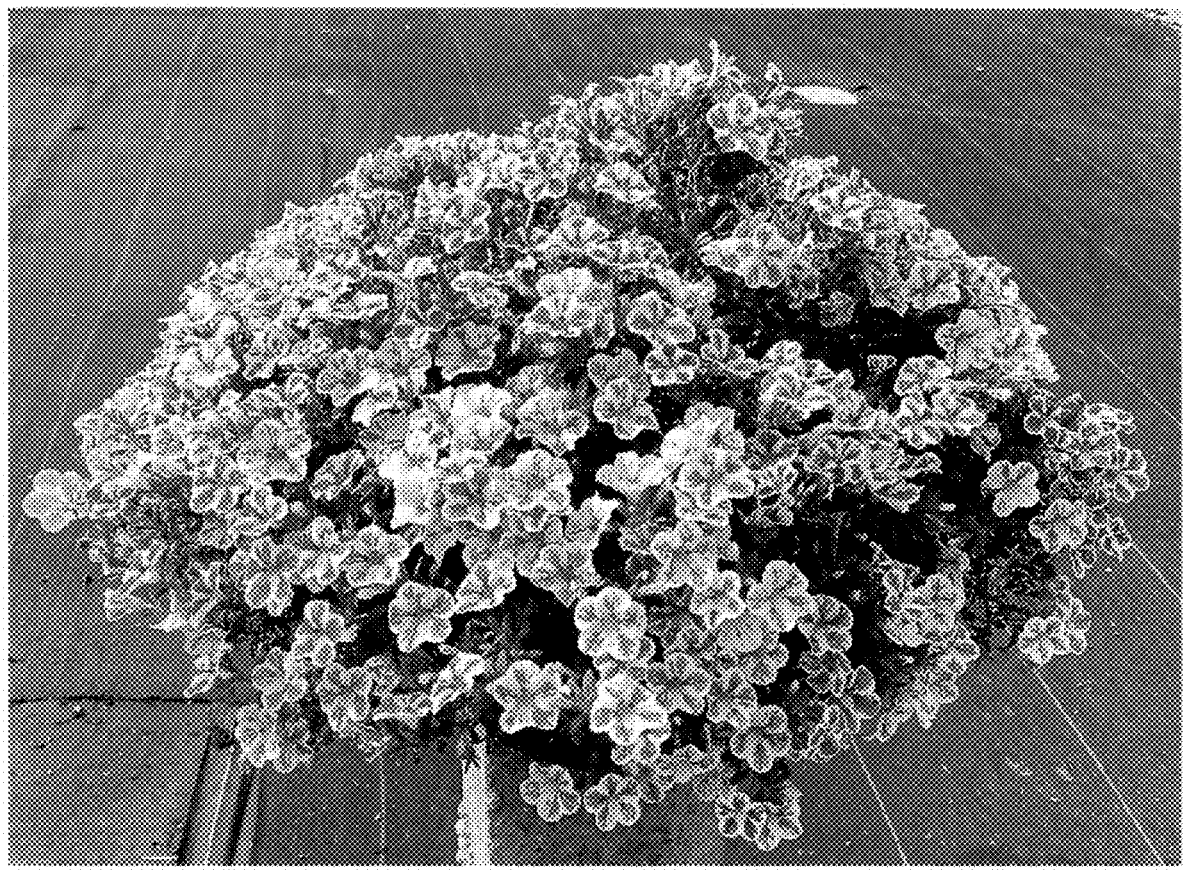
FIG. 1 illustrates a side view of the overall growth and flowering habit of 'Balchaelink'.
Figure 2:
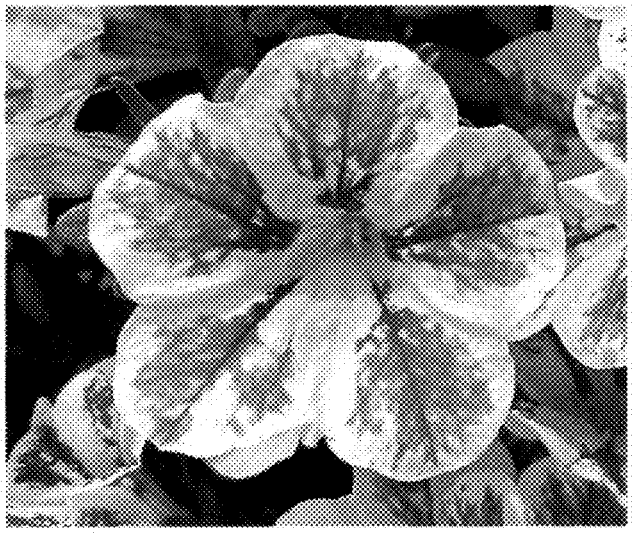
FIG. 2 illustrates a close-up view of an individual flower of 'Balchaelink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2023 under natural light conditions in West Chicago, Ill.

The following descriptions and measurements describe approximately 4-month-old plants produced from cuttings from stock plants and grown under conditions comparable to those used in commercial practice. The plants were grown in West Chicago, Illinois in 3-gallon pots utilizing a soilless growth medium for approximately 8 weeks in an outdoor nursery in West Chicago, Ill. Plants were given three pinches prior to transplant. Eight weeks after cuttings were stuck, plants were sprayed with growth regulators B-NINE (daminozide [butanedioic acid mono (2,2-dimethylhydrazide)]) at 2,500 ppm and CYCOCEL (chlormequat (2-chloroethyl) trimethylammonium chloride) at 800 ppm. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used during propagation stage. Measurements and numerical values represent averages of typical plants.

Botanical classification: *Calibrachoa* x *hybrida* 'Balchaelink'.

Parentage:

*Female parent*.—Proprietary *Calibrachoa* x *hybrida* breeding selection coded CAL-16249-01, not patented.

*Male parent*.—SUPERBELLS Holy Cow! 'BBCAL85303', U.S. Plant Pat. No. 30,840.

Propagation:

*Type cutting*.—Terminal stem.

*Time to initiate roots*.—Approximately 6 to 8 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 9 weeks from a rooted cutting to finish in a 10 cm pot.

*Growth habit and general appearance*.—Vigorous, mounded-trailing.

*Size*.—Height from soil level to top of plant plane: Approximately 24.0 cm. Width: Approximately 64.0 cm.

*Branching habit*.—Freely branching, pinching enhances basal branching. Quantity of branches per plant: Approximately 6 basal branches with laterals at potentially every node.

*Lateral branch*.—Strength: Moderate. Length: Approximately 11.5 to 20.0 cm. Diameter: Approximately 2.0 mm to 5.0 mm. Length of central internode: Approximately 1.5 cm. Texture: Densely pubescent. Color of young stems: 146D. Color of mature stems: 146C, becoming woody 199B with age.

Foliage description:

*General description*.—Fragrance: None detected. Form: Simple. Arrangement on flowering stem: Opposite.

*Leaves*.—Aspect: At acute angle to stem with tip turning downward. Shape: Elliptic. Margin: Entire. Apex: Broadly acute. Base: Attenuate. Venation pattern: Pinnate. Length of mature leaf: Approximately 2.9 cm. Width of mature leaf: Approximately 9.0 mm. Texture of upper and lower surfaces: Densely glandular pubescent. Gland color: Colorless, transparent. Color of upper surface of young and mature foliage: 137A with midvein of 146C. Color of lower surface of young and mature foliage: Closest to 138A with midvein of 146D.

*Petiole*.—Length: Approximately 2.0 mm. Diameter: Approximately 1.0 mm. Texture: Densely glandular pubescent. Gland color: Colorless, transparent. Color: 146D.

Flowering description:

*Flowering habit*.—'Balchaelink' is freely flowering under outdoor growing conditions with substantially continuous blooming from spring through autumn and year-round in greenhouse environment.

*Lastingness of individual flower on the plant*.—Approximately 5 to 7 days.

Flower description:

*General description*.—Type: Single, salverform. Quantity per plant: Approximately 250 Fragrance: None detected.

*Bud*.—Rate of opening: Generally takes 3 to 4 days for bud to progress from first color to fully open flower. Quantity per plant: Approximately 100.

*Bud just before opening*.—Shape: Oblong. Length: Approximately 1.9 cm. Diameter: Approximately 5.0 mm. Texture: Densely glandular pubescent. Gland color: Colorless, transparent. Color: 1C with venation of N77A.

*Corolla*.—Diameter: Approximately 3.8 cm.

*Petals*.—Quantity: 5, fused to form a tube. Shape: Obovate. Margin: Entire. Apex: Cuspidate to obtuse. Length from tube: Approximately 1.6 cm. Length of free portion: Approximately 9.0 mm. Intensity of flower lobing: Strong. Width: Approximately 1.8 cm. Texture of upper surface: Glabrous. Texture of lower surface: Moderately glandular pubescent, dense along venation. Gland color: Colorless, transparent. Color of upper surface when first open: NN155D with irregular centers of NN78A mottled with NN155D; 7A to 7B at throat opening not in an "eye" pattern; faint midveins of N77A. Color of lower surface when first and fully open: NN155D with irregular centers of NN78D mottled with NN155D; midveins of N77A. Color of upper surface when fully open: NN155D with irregular centers of NN78A mottled with NN155D; 7B to 7C at throat opening not in an "eye" pattern; faint midveins of N77A. Under more temperature growing conditions, NN155D can be limited to petal margins and not observed within the upper surface NN78A centers or lower surface NN78D centers.

*Corolla tube*.—Length: Approximately 1.7 cm. Diameter at distal end: Approximately 6.0 mm. Diameter at proximal end: Approximately 1.0 mm. Texture of inner surface: Glabrous. Texture of outer surface: Densely glandular pubescent. Gland color: Colorless, transparent. Color of inner surface: 13A with venation of N77A. Color of outer surface: 8B to 8C mottled with NN78D at distal end, venation of N77A.

*Sepals*.—Quantity per flower: 5, fused at base. Shape: Lanceolate. Apex: Acute. Length: Approximately 1.3 cm. Width: Approximately 3.0 mm. Texture of upper and lower surfaces: Densely glandular pubescent. Gland color: Colorless, transparent. Color of upper surface: 137B. Color of lower surface: 137B with base of 146D.

*Peduncle*.—Strength: Strong, flexible. Aspect: Acute angle to stem. Length: Approximately 1.5 cm. Diameter: Approximately 1.0 mm. Texture: Densely glandular pubescent. Gland color: Colorless, transparent. Color: 146C tinted with N186A.

*Reproductive organs*.—Androecium: Stamen quantity: 5, basifixed. Stamen length: Approximately 9.0 mm to 1.1 cm. Filament length of fixed portion: Approximately 4.0 mm. Filament color: 150D. Anther shape: Bilobed, ovoid. Anther length: Approximately 1.0 mm. Anther color: 8B. Pollen amount: Abundant. Pollen color: 8C. Gynoecium: Pistil quantity: 1 per flower. Pistil length: Approximately 1.1 cm. Stigma shape: Funnel. Stigma length: Approximately 1.0 mm. Stigma color: 144A. Style length: Approximately 8.0 mm. Style color: 145D. Ovary diameter: Approximately 2.0 mm. Ovary color: 144B.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balchaelink', substantially as herein illustrated and described.

* * * * *